United States Patent [19]
Qinghong et al.

[11] Patent Number: 6,046,330
[45] Date of Patent: Apr. 4, 2000

[54] COMPLEXES OF ULTRAVIOLET ABSORBERS AND QUATERNARY AMMONIUM COMPOUNDS WHICH ARE SUBSTANTIALLY FREE FROM UNWANTED SALTS

[76] Inventors: Jessica Ann Qinghong; Edward Zhao Ziaodong, both of 211 Windswept Ct., Moore, S.C. 29369

[21] Appl. No.: 09/065,618

[22] Filed: Apr. 24, 1998

[51] Int. Cl.$^7$ ................................................. C07D 239/42
[52] U.S. Cl. ............................ 544/327; 442/59; 562/46; 562/47; 564/149; 564/150
[58] Field of Search ............................. 442/59; 544/327; 562/46, 47; 564/149, 450

[56] References Cited

U.S. PATENT DOCUMENTS

| | | | |
|---|---|---|---|
| 4,340,389 | 7/1982 | Nonn et al. | 8/620 |
| 4,369,041 | 1/1983 | Dvorsky et al. | 8/532 |
| 4,383,948 | 5/1983 | Müller et al. | 260/459 A |
| 4,459,130 | 7/1984 | Helling et al. | 8/554 |
| 4,507,407 | 3/1985 | Kluger et al. | 521/113 |
| 4,563,190 | 1/1986 | Töpfl | 8/524 |
| 4,640,690 | 2/1987 | Baumgartner et al. | 8/506 |
| 4,648,883 | 3/1987 | Podder | 8/527 |
| 4,702,744 | 10/1987 | Wolff et al. | 8/527 |
| 5,059,244 | 10/1991 | King et al. | 106/21 |
| 5,098,445 | 3/1992 | Hung et al. | 8/507 |
| 5,221,288 | 6/1993 | Kamata et al. | 8/554 |
| 5,250,107 | 10/1993 | Bares | 106/20 R |
| 5,266,077 | 11/1993 | Auten et al. | 8/507 |
| 5,330,672 | 7/1994 | Langer et al. | 252/108 |
| 5,356,441 | 10/1994 | Tokieda et al. | 8/543 |
| 5,376,304 | 12/1994 | Yamamoto et al. | 252/309 |
| 5,399,692 | 3/1995 | Hung et al. | 544/327 |
| 5,403,358 | 4/1995 | Aston et al. | 8/445 |
| 5,500,024 | 3/1996 | Hung et al. | 8/509 |
| 5,811,111 | 9/1998 | McAtee et al. | 424/401 |

OTHER PUBLICATIONS

Surface Vehicle Recommended Practice, "(R) Accelerated Exposure of Automotive Interior Trim Components Using a Controlled Irradiance Water Cooled Xenon–Arc Apparatus, The Engineering Society For Advancing Mobility Land Sea Air and Space" (Mar., 1992).

AATCC Test Method 147–1993, "Antibacterial Activity Assessment of Textile Materials: Parallel Streak Method".

AATCC Test Method 76–1995, "Electrical Resistivity of Fabrics".

*Primary Examiner*—Helen L. Pezzuto
*Attorney, Agent, or Firm*—Terry T. Moyer; William S. Parks

[57] ABSTRACT

This invention relates to complexes of ultraviolet absorbers with quaternary ammonium compounds which are substantially free from unwanted salts. Such complexes are formed through ionic bonds formed between the two compounds. The inventive complexes are then removed of substantially all excess inorganic salt so as to obtain an UV absorber compound which exhibits improved light- and washfastness properties, which easily coats subject surfaces, which provides excellent non-fogging and non-cracking characteristics, and which also possesses anti-static, anti-microbial, and anti-abrasion properties. This invention also concerns methods of making and utilizing such inventive ultraviolet absorbing complexes.

15 Claims, No Drawings

text continues below …

COMPLEXES OF ULTRAVIOLET ABSORBERS AND QUATERNARY AMMONIUM COMPOUNDS WHICH ARE SUBSTANTIALLY FREE FROM UNWANTED SALTS

FIELD OF THE INVENTION

This invention relates to complexes of ultraviolet absorbers with quaternary ammonium compounds which are substantially free from unwanted salts. Such complexes are formed through ionic bonds formed between the two compounds. The inventive complexes are then removed of substantially all excess inorganic salt so as to obtain an UV absorber compound which exhibits improved light- and washfastness properties, which easily coats subject surfaces, which provides excellent non-fogging and non-cracking characteristics, and which also possesses anti-static, anti-microbial, and anti-abrasion properties. This invention also concerns methods of making and utilizing such inventive ultraviolet absorbing complexes.

BACKGROUND OF THE PRIOR ART

All of the patents cited throughout this specification are hereby entirely incorporated herein.

Quaternary ammonium compounds are well known as complexing agents for certain compounds, such as anionic dyes. For example, U.S. Pat. No. 5,059,244, to King, discloses an aqueous solution of anionic dyes and an ethoxylated triethanolamine. This composition is useful as an ingredient within ink formulations and as an agent for temporarily tinting textile fibers. Quaternary ammonium compounds have been disclosed as useful auxiliary agents for printing on fiber materials. For example, U.S. Pat. No. 3,785, 767, to Hildebrand, discloses a pad-steaming process for the continuous dyeing and printing of fiber material with a formulation containing anionic dyes and amine salts. Other pertinent teachings of include U.S. Pat. No. 4,563,190, to Topfl, which discloses a dyeing assistant formulation for anionic dyes containing quaternary ammonium compounds that contain at least one basic nitrogen atom to which are attached at least one polyglycol ether chain; U.S. Pat. No. 4,935,033, to Mosimann et al., which discloses a dyeing method for natural polyamide fibers using reactive dyes and a dyeing assistant agent containing a quaternary ammonium compound; and U.S. Pat. No. 4,369,041, to Dvorsky et al., discloses a technique for printing textiles involving exposing the textile to the action of quaternary ammonium compounds before or during the dyeing or printing with acid dyes. Furthermore, Aston et al., U.S. Pat. No. 5,403,358, discloses a pretreatment composition for ink jet which comprises a quaternary ammonium compound and a reactive dye. Such anionic dyes and quaternary ammonium compounds also find application in other areas, for instance: U.S. Pat. No. 4,459130, to Helling et al., discloses a dye preparation which is consisted of an acid dye and a basic carrier which contains quaternary ammonium or phosphonium groups; and U.S. Pat. No. 5,266,077, to Auten et al., discloses a method for tinting a hydrophilic contact lens through the action of a quaternary ammonium compound as a dye complexing agent.

However, there is no teaching specifically complexing a known ultraviolet absorber with a quaternary ammonium compound to form a more versatile UV absorber, not to mention there is no teaching of such a complex which is substantially free from unwanted salts. The closest prior art, U.S. Pat. No. 5,376,304, to Yamamoto et al., discloses a ceric oxide sol (no UV absorber, but it ultimately performs a UV absorption function) which is basically a complex of an anionic compound which is substantially salt-free and a ceric oxide which is, possibly, further reacted with what may be a quat compound. If such a reaction does take place, patentee does not teach nor fairly suggest the performance of a subsequent post-quat reaction salt removal procedure. Furthermore, patentee's initial salt-free anionic compound is not an ultraviolet absorbing compound; however, the resultant ceric oxide sol does exhibit ultraviolet absorption properties.

It has been found that the complexation of an ultraviolet absorber with a quaternary anmmonium compound and the subsequent removal of substantially all the excess salt (formed from the reaction between the cation of the anionic UV absorber and the counter-ion of the quat) produces a compound which possesses the highly desired and unexpected characteristics such as, merely as non-limiting examples, lower incidences of cracking and improved fogging properties. Traditional UV absorbers, such as benzotriazole and benzophenone derivatives, are present on coated substrates as small organic molecules. When dispersed within coating compositions, such traditional absorbers tend to separate from the coating over time and crystallize within the coating on the target substrate. This potential for recrystallization by the traditional UV absorbing compounds thus would cause disassociation of the coating itself through cracking. Furthermore, standard UV absorbers readily sublimate from substrate coatings and produce "fog" which accumulates on other nearby surfaces. Undesirable lightly opaque films form on such surfaces (i.e., the inside of car windows) after a certain length of time of application of the absorber. Such cracking and fogging both diminish the aesthetics of the subject substrate (such as apparel, or upholstery, or the like) and could produce unwanted films on surrounding surfaces. It has been found that the complexation between an ultraviolet absorber and a quat compound provides a compound, upon further removal of substantially all unwanted salt, will not produce such problematic incidences as cracking or fogging on the coated subject substrate. Also, the inventive complex is easily dispersed and dissolved within any standard UV absorber coating composition. Additionally, the presence of such a quat component unexpectedly provides other benefits including anti-static and anti-microbial properties. Therefore, through the utilization of inexpensive reactions and quaternary ammonium compounds, the cost of providing a non-fogging, anti-static, anti-microbial, uniform film-forming, ultraviolet absorbing compound for myriad substrates can be greatly reduced. Therefore, it has been found that substantially salt-free UV absorber/quaternary ammonium complexes provide a cost-effective method of providing a great deal of highly desirable and beneficial properties to many different substrates.

When placed in a complexing solution, the ultraviolet absorber and the quaternary ammonium show a great affinity for one another such that upon disassociation with their respective cations and/or counter ions, the complexation of the absorber and quat drives the formation of unwanted excess salts comprised of the free cations and counter ions. Once the salts are formed, they are easy to remove through standard filtration, phase separation, or extraction techniques. These salts are generally inorganic in nature, although organic cations and counter-ions may also be present and thus should be substantially removed from the inventive complex. Such a salt removal ensures the absorber and quat will remain in a complex together rather than potentially reacting with free cation and/or counter ion upon disassociation within the resultant UV absorber solution. Thus, the desired properties are obtained with a greater amount of the absorber/quat complex and a much lower amount of residual unwanted salt. The term "substantially salt-free" is thus intended to mean free from such unwanted cation/counter-ion salts.

OBJECTS OF THE INVENTION

It is therefore an object of this invention to provide a substantially salt-free complex of ultraviolet absorbers and quaternary ammonium compounds, as improved UV absorbing compounds for various substrates and media. A further objective of this invention is to provide an ultraviolet absorbing compound which can be used for the treatment of textile, paper, wood, and any other surfaces which are exposed to photo-degradations.

SUMMARY OF THE INVENTION

Substantially salt-free ultraviolet absorber/quat complexes, and, more importantly, the advantages and applications of such substantially salt-free complexes have heretofore been unexplored. Anionic UV absorbers, which are the preferred types within the inventive complex might contain a certain amount of inorganic or organic salts. As discussed in greater detail below, such salts are also byproducts from the complexation between anionic UV absorbers and quaternary ammonium compounds. With the presence of such salts in the composition, either the quaternary ammonium compounds or the inorganic cations may serve as counter ions for the complexed anionic absorbers. As a result, the chances for continued complexation between the absorber and quat components decreases with the presence of increased amounts of inorganic salts. Since the UV absorber and quat compounds will disassociate in solution, some free anionic UV absorber will inevitably bond to free cations and some free quat will inevitably bond with free counter ions, thereby lowering the overall lightfastness, non-fogging, and non-migratory effect of the absorber/quat complex. This deleterious effect is thus more pronounced upon greater amounts of residual inorganic salt. Thus, salt-containing heterogeneous UV absorber/quat complex systems show uneven solubility, poor coating, and the like, in different substrate treatments. Such complexes are therefore unsuitable as UV absorbing compounds.

It has been discovered that a substantially salt-free anionic ultraviolet absorber/quaternary ammonium complex colorant, provides favorable migration, anti-fogging, anti-static, anti-microbial, uniform film-forming, and lightfastness characteristics as a treatment agent for textiles, paper, wood, plastics, and the like. Uniform films of UV absorbers are highly desired because such films resist cracking, do not build up or accumulate in discrete areas of subject substrates, and are not prone to degradation, and thus do not create "fog." The removal of inorganic salts provides an improved stability for the complexes. Furthermore, the aforementioned physical properties of the complex can be tailored to any particular requirement by altering the structure of the quaternary ammonium compound. For instance, a more hydrophobic quaternary ammonium structure affords the user, upon complexation with an anionic UV absorber and removal of substantially all of the resultant salt, an ultraviolet absorber which is more soluble within hydrophobic coating systems.

The inventive complexes can be used for providing extensive benefits, as those mentioned previously, to various different and diverse media and substrates. Virtually all types and classes of ultraviolet absorbers can be adopted to practice this invention; however, preferred as those which are anionic in nature. More preferred are those anionic absorbers which are based on benzotriazole, benzimidazole, triazine, or benzophenone systems, such as, as merely preferred examples, sulfonated hydroxybenzotriazole (trade name Cibafast® W), sodium 2-hydroxy-4-methoxy-5-sulfobenzophenone, 2-phenylbenzimidazole-5-sulfonic acid, and sodium 2,2'-dihydroxy-4,4'-dimethoxy-5,5'-disulfobenzophenone; most preferred is Cibafast® W, available from Ciba Geigy. Such UV absorbers are well known to possess desired absorption characteristics; however, they do not provide appreciable levels of anti-cracking, anti-fogging, anti-static, anti-abrasion, and/or anti-microbial benefits. Furthermore, as utilized in their pure, unaltered states, these compounds do not possess the requisite degree of lightfastness which is necessary for long-lasting single application (and thus cost-effective) ultraviolet protection. The cationic ammonium group bonds with free reactive groups (i.e., sulfonic and/or carboxylic acid) on the anionic UV absorber so as to form ionic bonds. It is not fully understood how the interaction between the cationic moiety of the quaternary ammonium and the anionic moieties of the absorber is accomplished; however, as discussed above, it is evident that the quaternary ammonium compound has a greater affinity for the anionic UV absorber rather than for the anionic counter ion to which such quats are generally bonded. The same holds true for the anionic UV absorber which has more of an affinity for the cationic quat rather than for the cationic counter ion. Upon complexation, then, as discussed extensively above, the free counter ions of both components react together to form the aforementioned unwanted salts which require removal (at least to a substantial extent) from the resultant complex in order to provide the desired beneficial properties. The permissible level of remaining salt, and thus the definition of substantially salt-free for this invention, within the inventive complex is, at most, about 5,000 ppm. In theory, it is impossible to remove all of the unwanted salt from such complexes; however, at such low, permissible, and attainable levels of salt content, the desired lightfastness, anti-fogging, anti-cracking, migration, anti-static, anti-microbial, and the like, characteristics may be obtained. Certainly, a level of no salt at all would be most preferred, although such a level is, as noted above, nearly impossible to achieve.

A wide range of quaternary ammonium compounds have been shown to be useful for practicing the invention. A broad list of potentially useful quats within this invention include trialkyl, dialkyl, dialkoxy alkyl, monoalkoxy, benzyl, and imidazolinium quaternary ammonium compounds. The particularly preferred quats are noted below as this is merely a broad list of different classes of quaternary ammonium compounds which may be useful within the inventive complex and method. By ways of example, and not limitation, a list of preferred classes and examples of quaternary ammonium compounds is set forth in the TABLE below:

TABLE 1

| Class | Example (description) |
| --- | --- |
| Trialkyl quats | Methyl tri(hydrogenated tallow) ammonium chloride |
| Dialkyl quats | Dicoco dimethyl ammonium chloride |
| Dialkoxy alkyl quats | Methyl bis(polyethoxyethanol) coco ammonium chloride |

TABLE 1-continued

| Class | Example (description) |
| --- | --- |
| Monoalkoxy quats | Methyl (polypropylene glycol) diethyl ammomium chloride |
| Benzyl quats | Dimethyl tallow benzyl ammonium chloride |
| imidazolinium quats | Methyl tallow amido-2-tallow imidazolinium methylsulfate |

Again, the examples listed above are merely preferred compounds as any such compound meeting the broadly listed classes of quats are within the scope of this invention. Further suitable quats worth mentioning, however, include tetraalkyl quats, mono-substituted polyalkoxyalkyl quats, di-substituted polyalkoxyalkyl quats, and tri-substituted polyalkoxyalkyl quats, again merely as examples. The amount of residual inorganic salts is generally between about 50 ppb and 5000 ppm. Typically sodium counter ions, and thus sodium salts, are the residual inorganic ions and salts within such anionic dyes. Monitoring of the inorganic salt level is available through conveniently and easily performed measurements of the sodium ion level within the composition. Additionally, the existence of such substantially salt-free UV absorber complexes provides an ease in handling, particularly with a liquid composition, during applications to substrates and media which is not as evident with standard UV absorbers.

Various purification techniques may be performed in order to remove substantially all of the residual unwanted salts from the complexes. Such techniques include, but are not limited to, solvent extraction, phase separation, ultrafiltration, and other filtration methods. Particularly preferred are ultrafiltration under high pressure, phase separation through the utilization of an ammonium carbonate rinsing procedure (i.e., three consecutive washings with 25% aqueous ammonium carbonate in a 1:1 weight ratio to complex), and solvent extraction filtration through the utilization of methylene chloride, chloroform, or the like. After the removal of excess inorganic salt, the resultant solution should also be stripped of excess water in order to purify the ultraviolet absorber complex.

Basically, then, the simplest manner of practicing the invention is first determine the desired UV absorber for its absorption performance, lightfastness, thermal stability, and the like, characteristics for the subject substrate to be coated; second, select the appropriate quaternary ammonium compound for the subject substrate based on the necessarily required physical properties such as migration, uniform dispersion, solubility, washfastness, and the like; third, react the two together to form a complex; and last, remove the unwanted salts from the complex.

DESCRIPTION OF THE PREFERRED EMBODIMENT

Without limiting the scope of the invention, the preferred features of the invention are exemplified below.

Synthesis of UV Absorbing Complex

EXAMPLE 1

Three parts of sulfonated hydroxybenzotriazole (trade name Cibafast W) and four parts of bis(hydrogenated tallow alkyl)-dimethyl quaternary ammonium chloride, available from Akzo Nobel Chemicals under the trade name Arquad® 2HT-75, were dissolved into 10 parts of water/methanol solution (5/1, v/v). The solution was stirred for 2–3 hours. The polymeric UV absorbers was purified through phase separation and chloroform extraction. The purified particulate polymeric UV absorber was then dispersed into water.

EXAMPLE 2

Thirty-three parts of sodium 2-hydroxy-4-methoxy-5-sulfobenzophenone and 92 parts of methylpolyoxyethylene (15) coco ammonium chloride (available from Witco under the trade name Variquat® K1215) were dissolved in 200 parts of water. The solution was stirred for 2 hours and subsequently extracted with methylene chloride. The methylene chloride solution was then stripped under vacuum to afford a homogenous liquid.

EXAMPLE 3

Forty-eight parts of sodium 2,2'-dihydroxy-4,4'-dimethoxy-5,5'-disulfobenzophenone and 95 parts of Variquat® K1215 were dissolved in 200 parts of water. The solution was stirred for 2 hours and subsequently extracted with methylene chloride. The methylene chloride solution was stripped under vacuum to afford a homogenous liquid.

Applications for the Inventive Complex

EXAMPLE 4

Lightfastness

The water dispersion from EXAMPLE 1 was used in a textile treatment composition and procedure through a conventional padding process on 100% polyester automotive fabric. This polymeric UV absorber provided excellent UV protection for the textile substrates, was nonvolatile (and thus should not create any appreciable fogging), and also significantly improved the lightfastness of dyed fabrics. The table below presents a number of examples of the improvement of lightfastness by padding certain amounts of the UV absorber complex of EXAMPLE 1 into automotive fabrics. The automotive fabrics lightfastness testing was performed under the standard test procedures promulgated by General Motors and Chrysler, "Surface Vehicle Recommended Practice. (R) Accelerated Exposure of Automotive Interior Trim Components Using a Controlled Irradiance Water Cooled Xenon-Arc Apparatus," promulgated by The Engineering Society for Advancing Mobility Land Sea Air and Space International. The measurements within TABLE 2 indicate different color coordinates. The higher ^E* and ^H*, the better the result. The lower ^L* and ^C*, the better the result. The Examples listed within TABLE 2 below correspond to the following:

A—Control with no complex
B—0.5% complex owf (the total pad-on amount of UV absorber on the fabric)
C—1.5% complex owf
D—5.5% complex owf
E—6.5% complex owf
F—8.0% complex owf
G—10.0% complex owf The automotive fabrics lightfastness testing was performed under the standard test procedures promulgated by General Motors and Chrysler.

TABLE 2

| Example | Ê* | L̂* | Ĉ* | Ĥ* |
|---------|------|------|-------|------|
| A | 4.54 | 4.01 | −0.91 | 1.92 |
| B | 3.69 | 3.32 | −0.87 | 1.35 |
| C | 3.29 | 2.90 | −0.92 | 1.26 |
| D | 2.61 | 2.08 | −0.73 | 1.42 |
| E | 3.01 | 2.56 | −0.83 | 1.34 |
| F | 2.96 | 2.56 | −0.76 | 1.27 |
| G | 2.95 | 2.83 | −0.37 | 0.73 |

Certainly, the presence of any of the inventive UV absorber complex provides a significant improvement in lightfastness over non-treated fabric and the greater the amount of inventive complex, the better the result.

EXAMPLE 5

Anti-static Properties

The UV absorber of EXAMPLE 1 also provides anti-static, anti-microbial, and anti-abrasion properties. The two following tables show results from anti-static and anti-microbial studies. TABLE 3 shows the results of testing the Electrical Resistivity of Fabric under AATCC Test Method 76. The Examples listed within TABLE 3 below correspond to the following:

H—Control (warp)
I—Control (fill)
J—3.0% complex owf (warp)
K—3.0% comples owf (fill)
L—4.0% complex owf (warp)
M—4.0% complex owf (fill)
N—5.0% complex owf (warp)
O—5.0% complex owf (fill)

TABLE 3

Anti-static Testing

| Example | Conductivity (Amperes) | Resistivity ($\Omega/cm^2$) |
|---------|------------------------|------------------------------|
| H | $5.240 \times 10^{-12}$ | $3.82 \times 10^{13}$ |
| I | $5.560 \times 10^{-12}$ | $3.60 \times 10^{13}$ |
| J | $1.620 \times 10^{-10}$ | $1.23 \times 10^{12}$ |
| K | $1.370 \times 10^{-10}$ | $1.46 \times 10^{12}$ |
| L | $2.100 \times 10^{-10}$ | $9.52 \times 10^{11}$ |
| M | $2.850 \times 10^{-10}$ | $7.02 \times 10^{11}$ |
| N | $3.280 \times 10^{-10}$ | $6.10 \times 10^{11}$ |
| O | $3.360 \times 10^{-10}$ | $5.95 \times 10^{11}$ |

Thus, the treated samples exhibited improved and beneficial anti-static properties as compared to the untreated fabric.

EXAMPLE 6

Anti-microbial Results

The anti-microbial characteristics of the inventive complex were tested using AATCC Test Method 147-1996 for growth-free zones and contact inhibition of Staphyloccocus aureus. The zone of inhibition indicates the migratory anti-microbial properties around the treated substrate. The contact inhibition test indicates the effectiveness of the anti-microbial agent on direct contact. The Examples listed within TABLE 2 below correspond to the following:

P—Control (face)
Q—Control (back)
R—1.2% complex owf (face)
S—1.2% complex owf (back)
T—0.9% complex owf (face)
U—0.9% complex owf (back)

TABLE 4

Anti-microbial Testing

| Example | Growth-Free Zone (mm) | Contact Inhibition (%) |
|---------|-----------------------|------------------------|
| P | 0.00 | 0.00 |
| Q | 0.00 | 0.00 |
| R | 0.00 | 100.00 |
| S | 0.00 | 100.00 |
| T | 4.00 | 100.00 |
| U | 1.00 | 100.00 |

Therefore, the inventive complex provides a certain degree of anti-microbial properties to treating fabrics as compared to untreated substrates.

EXAMPLE 7

Ultraviolet Absorption Characteristics

Of primary importance, however, the inventive UV absorber has proven effective in improving the sun protective factor (SPF) of fabrics. Ultraviolet (UV) radiation which has proven harmful to human skin includes the two different types known as UV-A, which falls within the range of 320–400 nm along the light spectrum, and UV-B, which is between 290–320 nm in wavelength. Any manner of reducing or preventing transmission of UV light thus must effectively block or absorb such radiation between these wavelengths (290 and 400 nm). An SPF number is measured by the following equation: 100/% transmission of UV light= SPF number. Thus, a composition permitting 20% transmission of UV light has a SPF# of 5; while a composition permitting 10% transmission has a SPF# of number of 10; and so on. The complex of EXAMPLE 1 was incorporated within a sample of Downy Care® fabric softener (5% of the total weight of the sample). The two fabrics used here are polycottons (peach-colored 65/35 polyester/cotton, V below, and purple-colored 65/35 polyester/cotton, W below). The results are tabulated as follows:

TABLE 5

Sun Protective Factor Measurements of Fabrics Treated With the Inventive Complex

| Example | SPF UV-A | UV-A Trans. | UV-B Trans. | % UV-A block | % UV-B block |
|---------|----------|-------------|-------------|--------------|--------------|
| V untreated | 6.5 | 15.30 | 2.90 | 84.70 | 97.10 |
| V treated | 9.9 | 10.10 | 2.70 | 89.90 | 97.30 |
| W untreated | 45.5 | 2.20 | 0.50 | 97.80 | 99.50 |
| W treated | 77.0 | 1.30 | 0.50 | 98.70 | 99.50 |

Therefore, the ultraviolet absorption of the treated fabrics increased upon contact with the inventive complex. It is noted that the above results were obtained by rinsing fabrics with the complex-containing Downy® fabric softener only once. It is expected that the corresponding SPF numbers for each treated example will continually increase upon multiple rinsing.

While specific features of the invention have been described, it will be understood, of course, that the invention is not limited to any particular configuration or practice since modification may well be made and other embodiments of the principals of the invention will no doubt occur to those skilled in the art to which the invention pertains. Therefore, it is contemplated by the appended claims to cover any such modifications as incorporate the features of the invention within the true meaning, spirit, and scope of such claims.

What is claimed is:

1. An ultra violet absorbing complex comprising the reaction product of
   an ultra violet absorber;
   and a quaternary ammonium compound;
   wherein said complex has been purified to substantially remove all salts other than the ultra violet absorber/quaternary ammonium complex.

2. The complex of claim 1 wherein
   the quaternary ammonium compound is selected from the group consisting essentially of trialkyl quats, dialkyl quats, dialkoxyalkyl quats, monoalkoxy quats, benzyl quats, imidazolinium quats, tetraalkyl quats, mono-substituted polyalkoxyalkyl quats, di-substituted polyalkoxyalkyl quats, tri-substituted polyalkoxyalkyl quats, and any mixtures thereof.

3. The complex of claim 2 wherein
   the quaternary ammonium compound is selected from the group consisting essentially of methyl tri(hydrogenated tallow) ammonium chloride, dicoco dimethyl ammonium chloride, methyl bis(polyethoxyethanol) coco ammonium chloride, methyl (polypropylene glycol) diethyl ammonium chloride, dimethyl tallow benzyl ammonium chloride, methyl tallow amido imidazolinium methylsulfate, and any mixtures thereof.

4. The complex of claim 2 wherein
   the ultraviolet absorber is an anionic ultraviolet absorber.

5. The complex of claim 4 wherein
   the anionic ultraviolet absorber is selected from the group consisting essentially of benzotriazoles, benzimidazoles, triazines, benzophenones, or mixtures thereof.

6. The complex of claim 5 wherein
   the anionic UV absorber is selected from the group consisting essentially of sulfonated hydroxybenzotriazole, sodium 2-hydroxy-4-methoxy-5-sulfo-benzophenone, sodium 2,2'-dihydroxy-4,4'-dimethoxy-5,5'-disulfobenzophenone, 2-phenylbenzimidazole-5-sulfonic acid, and mixtures thereof.

7. The complex of claim 6 wherein
   the anionic UV absorber is selected from the group consisting essentially of sulfonated hydroxybenzotriazole.

8. A thermoplastic or thermoset composition comprising the complex of claim 1.

9. A textile coated with the complex of claim 1.

10. A detergent composition comprising
    the complex of claim 1; and
    at least one surfactant.

11. A fabric softener composition comprising
    the complex of claim 1; and
    at least one textile softener compound.

12. A coating composition comprising
    the complex of claim 1; and
    at least one solvent.

13. The coating composition of claim 12 wherein
    said at least one solvent includes water.

14. The coating composition of claim 12 wherein
    said at least one solvent includes an organic solvent.

15. An ink formulation comprising the complex of claim 1; and at least one colorant.

* * * * *

UNITED STATES PATENT AND TRADEMARK OFFICE
CERTIFICATE OF CORRECTION

PATENT NO. : 6,046,330
DATED : April 4, 2000
INVENTOR(S) : Jessica Ann Qinghong; Edward Zhao Ziaodong It is certified that error appears in the above-identified patent and that said Letters Patent is hereby corrected as shown below:

On the inventor(s) line please delete: Jessica Ann Qinghong and Edward Zhao Ziadong Please replace with: Qinghong Jessica Ann and Ziaodong Edward Zhao Signed and Sealed this Thirtieth Day of January, 2001

Attest:

Q. TODD DICKINSON

*Attesting Officer*  *Director of Patents and Trademarks*